(12) United States Patent
Rauniyar et al.

(10) Patent No.: US 10,911,693 B2
(45) Date of Patent: Feb. 2, 2021

(54) GUIDANCE SYSTEMS AND ASSOCIATED METHODS

(71) Applicant: Boston Scientific Scimed, Inc., Maple Grove, MN (US)

(72) Inventors: Niraj P. Rauniyar, Plymouth, MN (US); Timothy P. Harrah, Cambridge, MA (US); Peter J. Pereira, Mendon, MA (US); William M. Asselin, Lunenburg, MA (US); Michael S. H. Chu, Brookline, MA (US); Brandon W. Craft, Edgewater, MD (US); Adam P. Nodiff, Southborough, MA (US); Chad Schneider, Owings Mills, MD (US); William Stanhope, Lunenburg, MA (US); Eric Wong, South Grafton, MA (US); Kimberly DeGraaf, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 428 days.

(21) Appl. No.: 15/808,272

(22) Filed: Nov. 9, 2017

(65) Prior Publication Data

US 2018/0139392 A1 May 17, 2018

Related U.S. Application Data

(60) Provisional application No. 62/420,891, filed on Nov. 11, 2016.

(51) Int. Cl.
*H04N 5/265* (2006.01)
*A61B 90/00* (2016.01)
(Continued)

(52) U.S. Cl.
CPC ......... *H04N 5/265* (2013.01); *A61B 1/00009* (2013.01); *A61B 1/04* (2013.01);
(Continued)

(58) Field of Classification Search
CPC ........ H04N 6/265; A61B 34/20; A61B 90/37; A61B 1/00009; A61B 1/04
(Continued)

(56) References Cited

U.S. PATENT DOCUMENTS 8,204,576 B2 6/2012 Ikuma et al.
8,244,495 B2 8/2012 Goldbach et al.
(Continued)

FOREIGN PATENT DOCUMENTS

WO WO 2007/002685 A2 1/2007

OTHER PUBLICATIONS

Gokce Gurun et al., "Single-Chip CMUT-on-CMOS Front-End System for Real-Time Volumetric IVUS and ICE Imaging," IEEE Trans Ultrason Ferroelectr Freq Control, Feb. 2014, 61(2):239-250 (Retrieved from NIH Public Access, 34 pages).

*Primary Examiner* — Howard D Brown, Jr.
*Assistant Examiner* — Kristin Dobbs
(74) *Attorney, Agent, or Firm* — Bookoff McAndrews, PLLC

(57) ABSTRACT

Guidance systems and associated methods are disclosed. One method comprises: receiving macroscan data prior to an operation; defining a body information model from the macroscan data; positioning a navigation component in the body during the operation; generating microscan data with the navigation component; correlating a location in the macroscan data with a location in the microscan data in the body information model; and/or modifying the body information model by combining an image in the microscan data with an image in the macroscan data.

20 Claims, 10 Drawing Sheets

(51) Int. Cl.
*A61B 34/20* (2016.01)
*A61B 1/00* (2006.01)
*A61B 1/04* (2006.01)
*A61B 1/06* (2006.01)
*A61B 5/06* (2006.01)
*A61B 8/12* (2006.01)
*A61B 8/08* (2006.01)
*H04N 5/225* (2006.01)
*A61B 90/30* (2016.01)
*A61B 34/10* (2016.01)

(52) U.S. Cl.
CPC ............ *A61B 1/063* (2013.01); *A61B 1/0676* (2013.01); *A61B 5/062* (2013.01); *A61B 8/12* (2013.01); *A61B 8/5207* (2013.01); *A61B 34/20* (2016.02); *A61B 90/37* (2016.02); *H04N 5/2256* (2013.01); *A61B 2034/105* (2016.02); *A61B 2034/2051* (2016.02); *A61B 2034/2061* (2016.02); *A61B 2034/2065* (2016.02); *A61B 2090/309* (2016.02); *A61B 2090/364* (2016.02); *A61B 2090/371* (2016.02); *A61B 2090/373* (2016.02); *A61B 2090/3784* (2016.02); *A61B 2090/3966* (2016.02); *H04N 2005/2255* (2013.01)

(58) Field of Classification Search
USPC .......................................................... 348/68
See application file for complete search history.

(56) References Cited

U.S. PATENT DOCUMENTS

| | | |
|---|---|---|
| 8,260,395 B2 | 9/2012 | Markowitz et al. |
| 8,517,924 B2 | 8/2013 | Banik et al. |
| 9,380,930 B2 | 7/2016 | Oskin et al. |
| 2007/0016029 A1 | 1/2007 | Donaldson et al. |
| 2012/0157844 A1 | 6/2012 | Halmann |
| 2014/0257095 A1 | 9/2014 | Kemp et al. |
| 2014/0343416 A1* | 11/2014 | Panescu ............... A61B 34/30 600/431 |
| 2015/0366534 A1 | 12/2015 | Nair et al. |
| 2018/0174311 A1* | 6/2018 | Kluckner ............ G06K 9/6259 |

* cited by examiner

GUIDANCE SYSTEMS AND ASSOCIATED METHODS

CROSS-REFERENCE TO RELATED APPLICATIONS

This application claims the benefit of priority to U.S. Provisional Application No. 62/420,891, filed Nov. 11, 2016, which is incorporated by reference herein in its entirety.

TECHNICAL FIELD

Aspects of the present disclosure generally relate to medical devices and operations. Particular aspects relate to guidance systems and associated methods.

BACKGROUND

Elongated devices are commonly used to access remote regions and cavities of the body for diagnostic, surgical, and/or therapeutic purposes. For example, endoscopes may use naturally formed lumens or orifices, and/or surgical incisions to access the colon, esophagus, stomach, urethra, bladder, ureter, kidneys, lungs, bronchi, uterus, and other organs; and catheters may use the circulatory system as pathways to access treatment sites near the heart, or the urinary canal to access urinary regions. These elongated devices may be introduced into the body through a natural body path, such as large artery, including those found in the groin or in the neck. The same device also may be introduced through artificial paths formed in the body, such as a tunnel formed by a tunneling tool.

Navigation through some body paths requires the elongated device to be passed through ever-narrowing diameters until a distal end of the device reaches an operative site inside the body. Locating the distal end at the operative site can be challenging. In some instances, a fluoroscope may be employed to guide the distal end through the body in one plane of movement. Because X-rays are applied externally, in a single imaging plane, they often cannot account for localized aspects of body paths, especially paths extending deep into the body. Additional sensing technologies are needed to guide medical devices through a greater range of body paths, and reduce the risks associated with such navigation. Aspects of the devices, methods, and systems described herein are provided to address these issues.

SUMMARY

Aspects of the present disclosure relate to guidance devices, systems, and methods. Numerous aspects of the present disclosure are now described.

One aspect of the present disclosure is a method comprising: receiving macroscan data including first images of a body and first location data associated with each first image; combining the first images according to the first location data to generate a body information model; positioning a navigation component in the body; generating microscan data with the navigation component, the microscan data including second images of the body and second location data associated with each second image; correlating the first location data with the second location data at a target location in the body information model; and/or modifying the body information model by combining the first images with the second images at the target location.

According to this aspect, the navigation component may include an elongated shaft and an internal scanner located on a distal portion of the elongated shaft, and the method may comprise positioning the internal scanner in the body, and generating the microscan data with the internal scanner. The internal scanner may include a probe configured to generate wave energy images of the body and the second images may include the wave energy images, the method further comprising generating the wave energy images with the probe. The probe may include one or more ultrasound transducers configured to generate ultrasound images of the body, and generating the wave energy images may comprise generating ultrasound images with the one or more ultrasound transducers. The probe may include one or more laser sources configured to generate laser images of the body, and generating the wave energy images may comprise generating laser images with the one or more laser sources.

In some aspects, the internal scanner may include a plurality of imaging elements configured to generate graphical images and the second images may include the graphical images, the method further comprising generating the graphical images at one or more frequencies of the electromagnetic spectrum with the plurality of imaging elements. Generating the graphical images may comprise generating the graphical images in a visual light range. The internal scanner includes a plurality of light sources, and the method may further comprise operating the plurality of light sources independent of or together with the plurality of imaging elements. Generating the microscan data may include generating second images and location data according to a predetermined sequence. For example, the second images may be generated at a rate of 60 Hz or greater in the predetermined sequence.

In other aspects, the navigation component may include an elongated shaft, and positioning a navigation component in the body may comprise moving a distal portion of the elongated shaft through the body. For example, the distal portion of the elongated shaft may include a tracking sensor responsive to a magnetic field, and generating second location data may comprise moving the sensor in the field.

Another aspect of the present disclosure is a method comprising: receiving macroscan data prior to an operation; generating a body information model from the macroscan data; positioning a navigation component in the body during the operation; generating microscan data with the navigation component; correlating a location in the macroscan data with a location in the microscan data in the body information model; and/or modifying the body information model by combining an image in the microscan data with an image in the macroscan data.

According to this aspect, the method may comprise outputting a portion of the body information model as a navigation image. For example, the method may comprise: identifying a path through the body in the navigation image; identifying a location of the navigation component in the navigation image; and guiding the navigation component along the path in the navigation image. The method may further comprise: locating objects in the body relative to the path; and guiding the navigation component to the located objects. In some aspects, the method includes determining characteristics of the located objects. The method also may include: selecting one of the located objects based on its characteristics; performing a treatment on the selected object; and modifying the body information model to indicate that the selected object has been treated.

Yet another aspect of the present disclosure is a method comprising: receiving macroscan data prior to an operation, the macroscan data including first images of a body and first location data associated with each first image; combining the first images according to the first location data to generate a body information model; positioning a navigation component in the body during the operation; generating microscan data with the navigation component, the microscan data including second images of the body and second location data associated with each second image; correlating the first location data with the second location data at a target location in the body information model; modifying the body information model by combining the first images with the second images at the target location; outputting a portion of the body information model as a navigation image; identifying a path through the body in the navigation image; identifying a location of the navigation component in the navigation image; and/or guiding the navigation component along the path in the navigation image.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure. Each drawing depicts one or more aspects of this disclosure as follows.

DETAILED DESCRIPTION

Aspects of the present disclosure are now described with reference to exemplary guidance systems and associated methods. Some aspects are described with reference to operations where an elongated device is guided through a body path until a distal end of the elongated body is located in a body cavity (or other target site in a body). For example, an endoscope may include an elongated body that is guided through a natural body path including a urethra, bladder, and/or ureter until a distal end of endoscope is located in an interior cavity of a kidney. References to a particular type of operation or procedure, such as medical; body path, such as natural or artificial; or body cavity, such as the interior cavity of a kidney, are provided for convenience and not intended to limit the present disclosure unless claimed. Accordingly, the concepts described herein may be utilized for any analogous device or method—medical or otherwise, kidney-specific or not.

Numerous axes are described. Each axis may be transverse, or even perpendicular, with the next so as to establish a Cartesian coordinate system with an origin point O (or O'). One axis may extend along a longitudinal axis extending through an origin point defined within an element or body path. The directional terms "proximal" and "distal," and their respective initials "P" and "D," may be used to describe relative components and features in relation to these axes. Proximal refers to a position closer to the exterior of the body or a user, whereas distal refers to a position closer to the interior of the body or further away from the user. Appending the initials "P" or "D" to an element number signifies a proximal or distal location, and appending P or D to an arrow in a figure signifies a proximal or distal direction along one or more axes. The term "elongated" may be used to describe any aspect extending proximally or distally along any axis. Unless claimed, these terms are provided for convenience and not intended to limit the present disclosure to a particular location, direction, or orientation.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements. As used herein, terms such as "about," "substantially," "approximately," or like variations, may indicate a range of values within +/−5% of a stated value.

Figure 1:
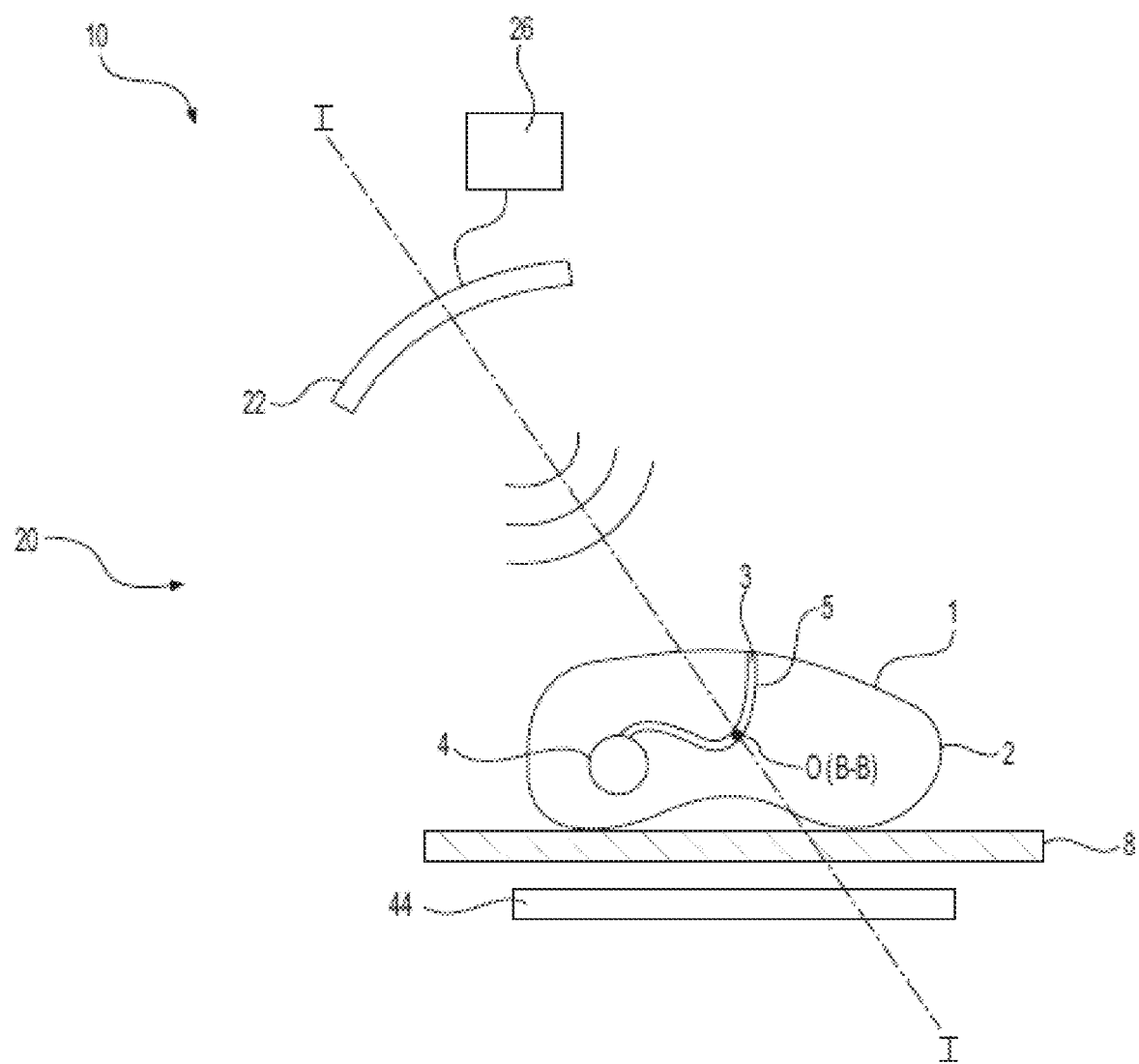
FIG. 1 depicts an exemplary mapping component of a system.

Aspects of the present disclosure pertain to an exemplary guidance system 10, examples of which are depicted in FIGS. 1-8B with reference to an exemplary body 1. Body 1 may be a patient's body (e.g., a human body) or a portion thereof. In FIG. 1, for example, body 1 is depicted as a medial-lateral cross-section of a human torso including: an exterior surface 2; an entry point 3 on surface 2; a body cavity 4; and a body path 5 extending between entry point 3 and cavity 4. A body axis B-B extends through an origin point O in body 1 (e.g., FIG. 1), and a body path P-P extends through an origin point O' in body path 5 (e.g., FIGS. 4A-B).

Figure 5:
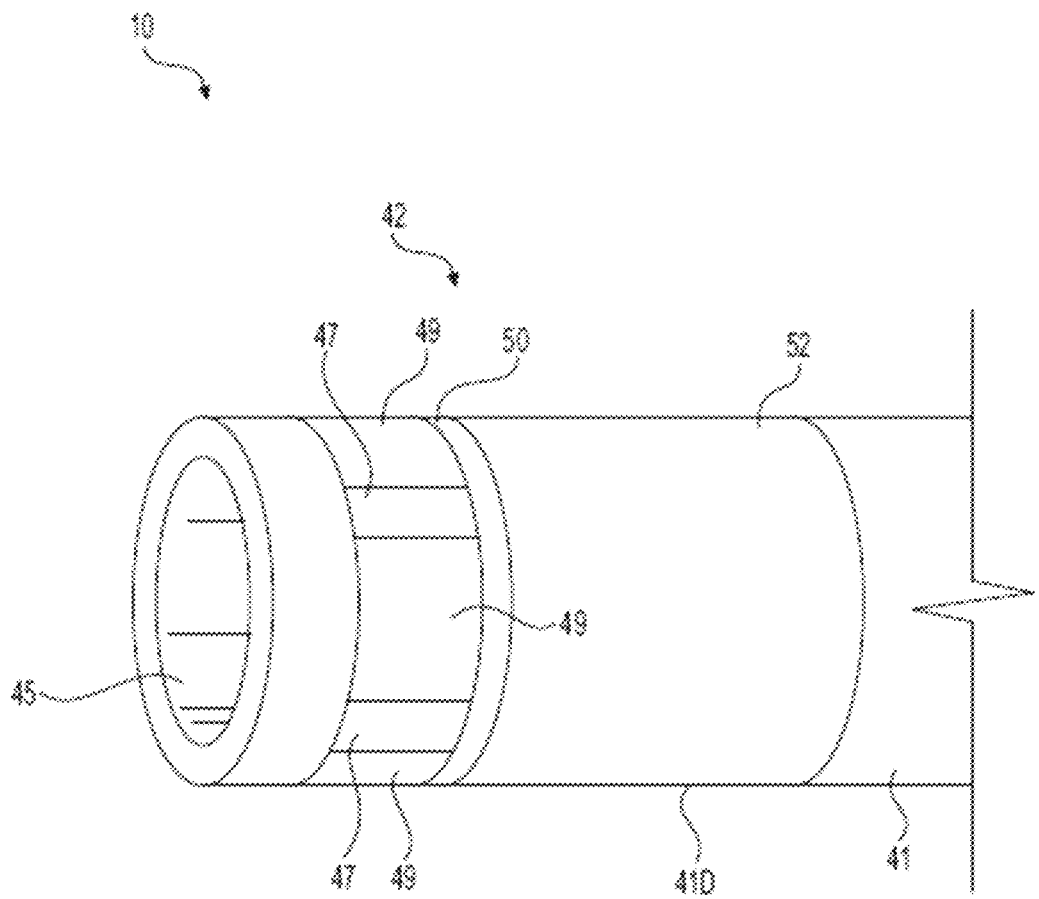
FIG. 5 depicts an exemplary configuration of the navigation component depicted in FIGS. 4A-B.
Figure 6A:
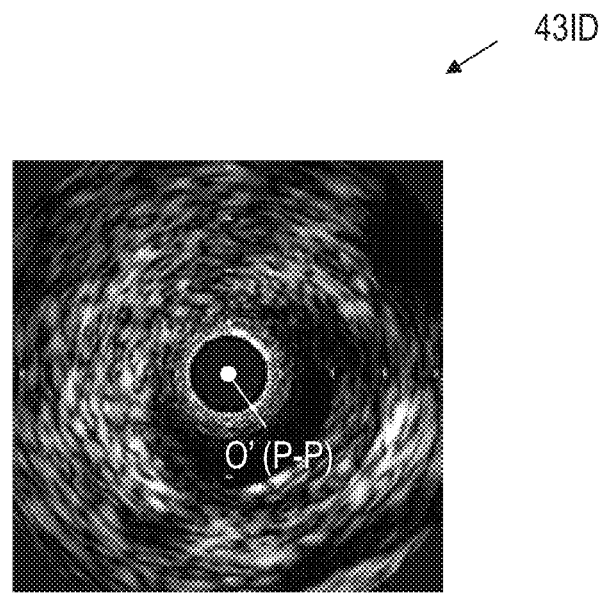
FIG. 6A depicts exemplary aspects of microscan data.
Figure 6B:
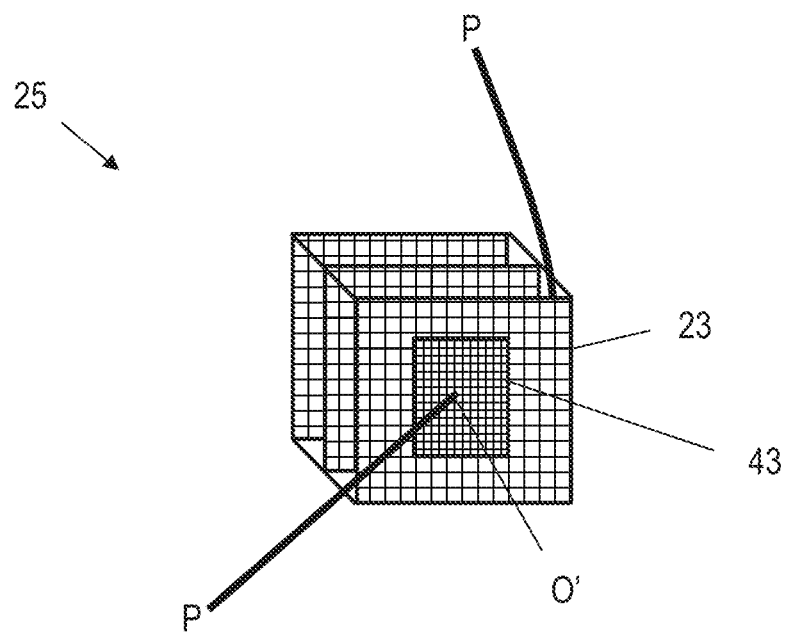
FIG. 6B depicts additional exemplary aspects of microscan data.
Figure 7:
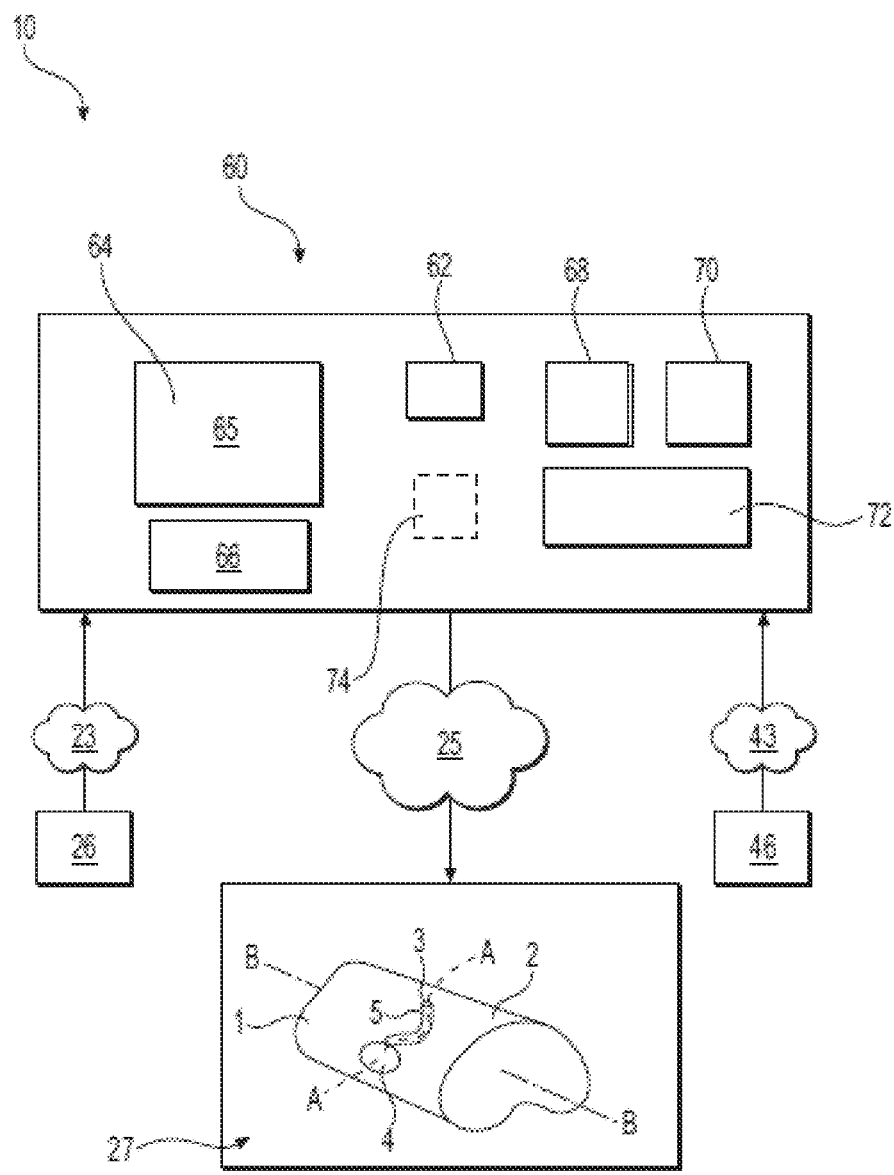
FIG. 7 depicts an exemplary controller.

System 10 may include: a mapping component 20 configured to perform microscans of body 1 (e.g., FIG. 1) and output macroscan data 23 (e.g., FIGS. 2A-B); a navigation component 40 configured to perform macroscans of body 1 (e.g., FIGS. 4A-5) and output microscan data 43 (e.g., FIGS. 6A-B); and a controller 60 (e.g., FIG. 7) configured to generate a pre-operative body information model 25 (e.g., FIG. 3) from macroscan data 23, operatively update information model 25 with microscan data 43, and/or output portions of model 25 as a navigation image 27 (e.g., FIG. 7). The terms "macroscan(s)" and "microscan(s)" are utilized herein to describe aspects of system 10. In this application, a macroscan may be obtained from an externally-applied scanning medium (e.g., X-rays from a CT scanner), while a microscan may be obtained from an internally-applied scanning medium (e.g., sound waves from a transducer).

Figure 2A:
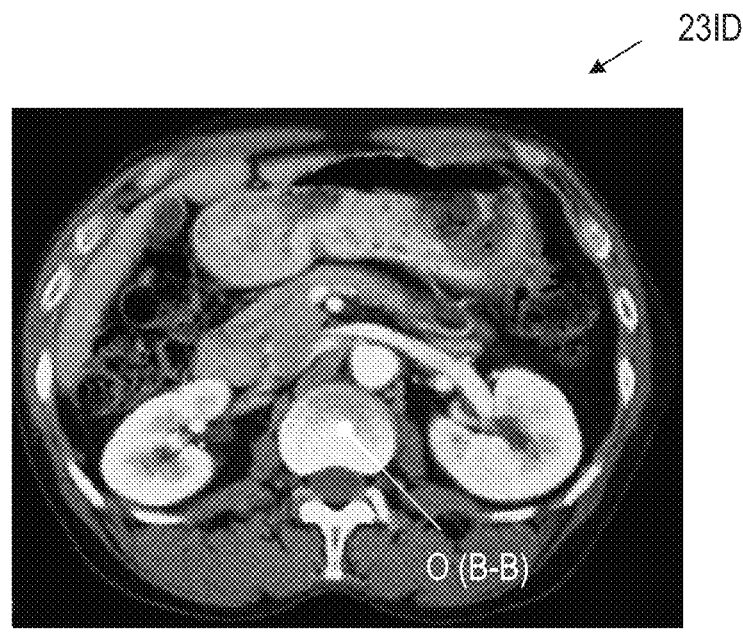
FIG. 2A depicts exemplary aspects of macroscan data.
Figure 2B:
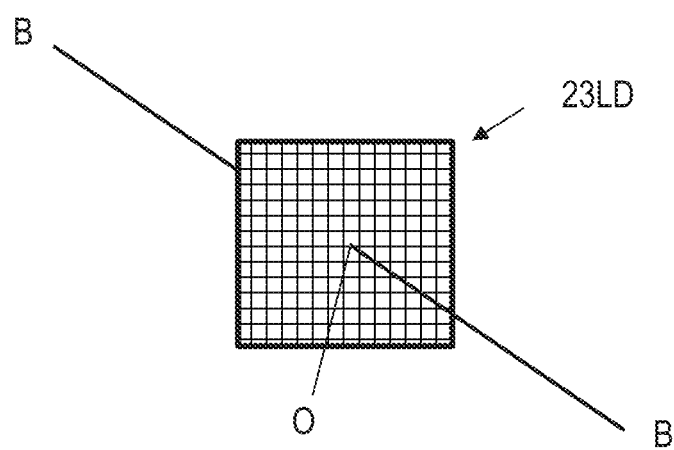
FIG. 2B depicts additional exemplary aspects of the microscan data.

Mapping component 20 is configured to perform macroscans of body 1, and output macroscan data 23. An exemplary mapping component 20 is depicted in FIG. 1 as comprising an external scanner 22 configured to take one or more macroscans of body 1, and a transmitter 26 configured to output macroscan data 23. As shown in FIGS. 2A-B, macroscan data 23 may include: imaging data 23ID (e.g., a wave energy image) generated from the macroscan; and location data 23LD (.e.g., the location of the wave energy image along body axis B-B) generated when the macroscan is performed.

Imaging data 23ID may include any number of two- or three-dimensional images generated by external scanner 22 in any format, at any resolution, using any scanning medium. For example, scanner 22 may be configured to direct a wave energy (e.g., light, sound, X-rays, etc.) toward exterior surface 2 of body 1, receive a reflected portion of the wave energy, and generate imaging data 23ID including wave energy images of body 1. In some aspects, scanner 22 may be a CT scanner configured to direct and receive X-rays along an imaging axis I-I, and generate imaging data 23ID including a plurality of two-dimensional cross-sectional X-ray images taken at one or more angles and/or positions relative to body 1. A representative cross-sectional X-ray image is depicted in FIG. 2A as imaging data 23ID generated by a CT scanner. Similar images may be created with other wave energies. In other aspects, external scanner 22 may include a magnetic resonance imaging device configured to use magnetic fields, radio waves, and field gradients to generate imaging data 23ID including a plurality of three-dimensional images.

Location data 23LD may be used to locate imaging data 23ID in body 1 with respect to natural and/or artificial markers. In FIG. 1, an imaging plane I-I extends through origin point O and body axis B-B extending therethrough. Origin point O may be defined at the centroid of a vertebrae of body 1 (e.g., FIG. 2A), allowing body axis B-B to coincide with a longitudinal axis extending through the spine of body 1, and provide a common point of reference in each macroscan. Artificial markers may alternatively be placed in or on body 1 to define the location of origin point O and/or body axis B-B. For example, an artificial marker may be placed on exterior surface 2, inside of body cavity 4, and/or on bed 8; and include radiopaque elements shaped to define the location of point O and/or axis B-B in a cross-sectional X-ray image of body 1.

Transceiver 26 may comprise any wired or wireless technology configured to output macroscan data 23. For example, transceiver 26 may be configured to output data 23 and/or otherwise communicate with a transceiver 66 of controller 60 using any known data communication technology, including Bluetooth®, fiber optic cables, Wi-Fi, and the like. If mapping component 20, navigation component 40, and controller 60 are all part of the same device, then transceiver 26 may simply be a direct or wired connection between the respective components of such a device.

Figure 4A:
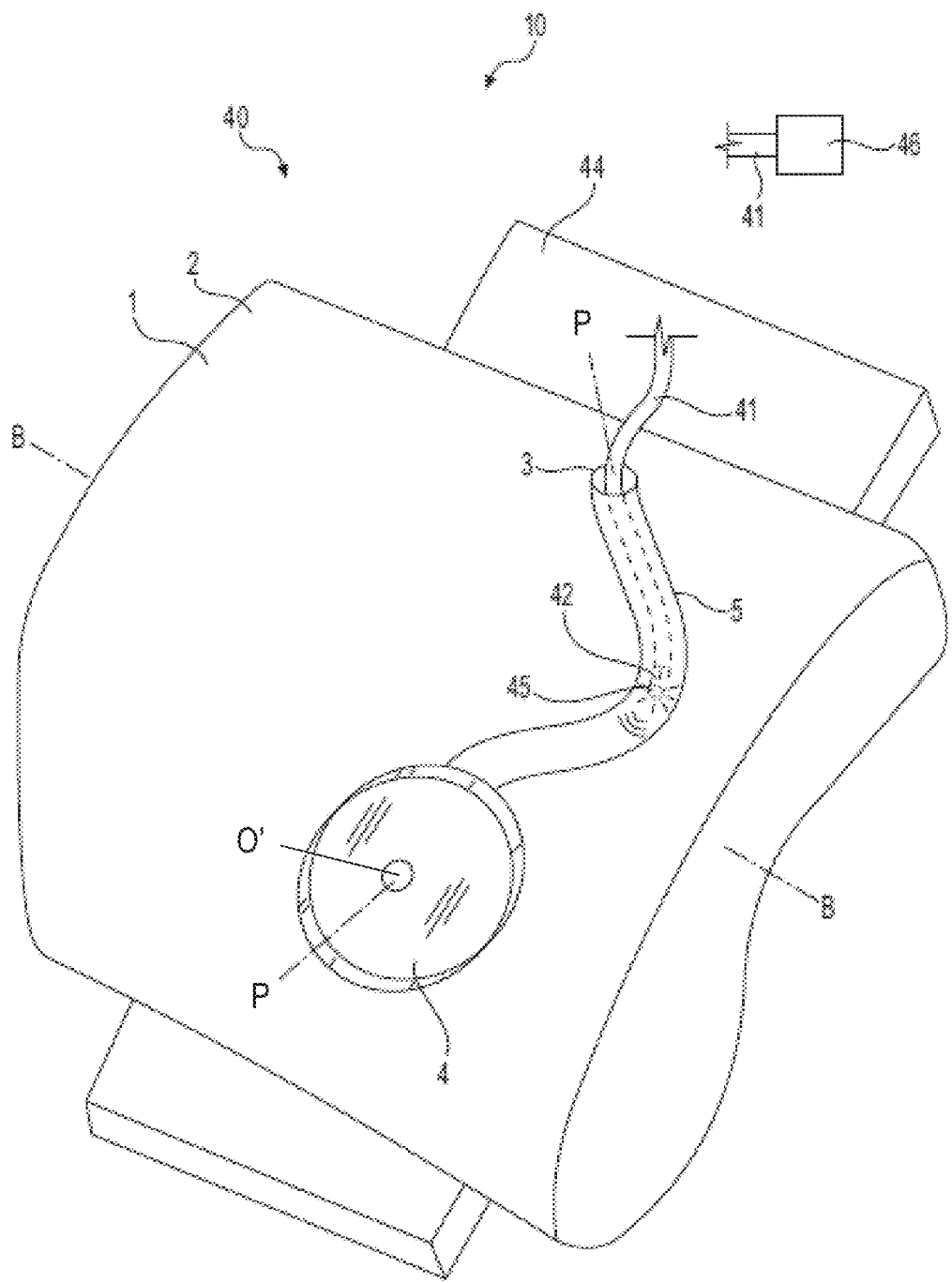
FIG. 4A depicts aspects of an exemplary navigation component at a first location in a body.

With reference to FIG. 4A, navigation component 40 is configured to perform microscans of body 1, and output microscan data 43. Numerous aspects of navigation component 40 are described. According to one aspect, depicted for example in FIGS. 4A-5, navigation component 40 may comprise: an elongated shaft 41 steerable through body path 5; an internal scanner or sensor 42 configured to perform one or more microscans as shaft 41 is moved along path 5; a magnetic field generator 44 configured to generate a magnetic field about path 5; a tracking sensor 50 configured to locate scanner 42 in the magnetic field; and a transceiver 46 configured to output microscan data 43. As shown in FIGS. 6A-B, microscan data 43 may include imaging data 43ID (e.g., a wave energy image) generated from the microscan, and location data 43LD (e.g., the location of the wave energy image along axis P-P) generated when the microscan is performed.

Figure 4B:
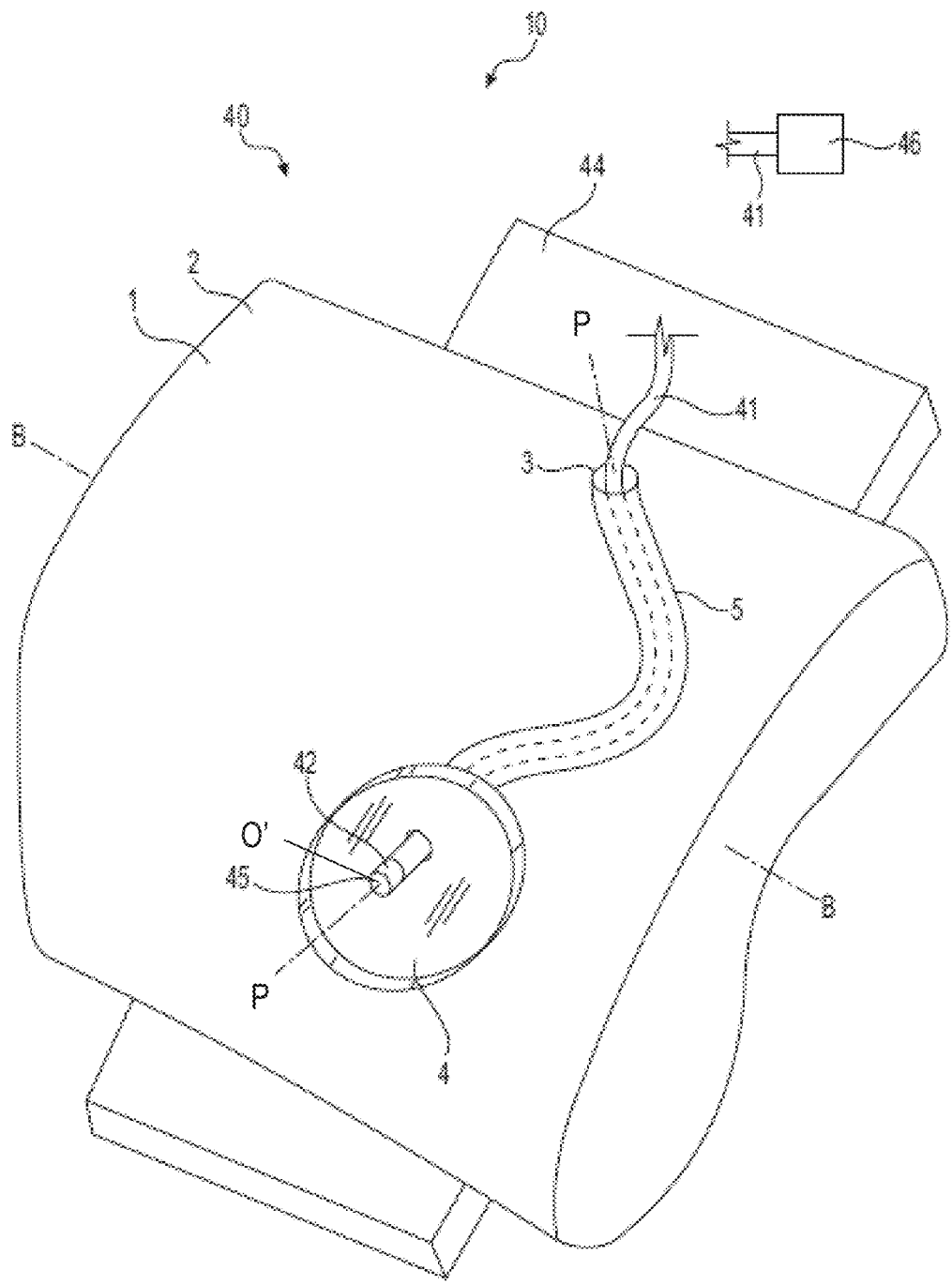
FIG. 4B depicts the navigation component of FIG. 2A at a second location in a body.

Elongated shaft 41 of FIGS. 4A-B may include at least one channel 45 extending therethrough, and any number of articulating portions and/or steering mechanisms operable together with channel 45. An exemplary steering mechanism may comprise a handle attached to a proximal end of shaft 41, and a plurality of pull wires extending through shaft 41, wherein the wires are configured to articulate shaft 41 in response to a physical force applied to an actuator on the handle, as in U.S. Pat. No. 9,380,930, issued Jul. 5, 2016, the entirety of which is hereby incorporated by reference. In other aspects, shaft 41 may include a plurality of electrically responsive articulation sections configured to articulate shaft 41 in response to a control signal from controller 60, as in U.S. Pat. No. 8,517,924, issued Aug. 27, 2013, the entirety of which is hereby incorporated by reference. For example, the control signal may be generated in response to a user input, such as the movement of a joystick or like input device, including those described in U.S. Provisional Patent Application No. 62/287,667, filed Jan. 27, 2016, the entirety of which is hereby incorporated by reference.

Imaging data 43ID may include any number of two- or three-dimensional images generated by internal scanner 42 in any format, at any resolution, using any scanning medium. For example, scanner 42 may be configured to generate imaging data 43ID including three-dimensional images generated with computed-tomography (CT), ultrasound, positron emission tomography (PET), and/or like techniques. The depth, quality, and/or resolution of imaging data 43ID may be different and/or greater than that of imaging data 23ID, as indicated by exemplary grid patterns depicted in FIGS. 2B and 6B respectively. An exemplary scanner 42 is depicted in FIG. 5. As shown, scanner 42 may be disposed on a distal portion 41D of shaft 41, and include a plurality of imaging elements 47; a plurality of light sources 49; and a probe 52. Each element of exemplary scanner 42 is now described.

The plurality of imaging elements 47 may be configured to generate a portion of imaging data 43ID. For example, data 43ID may be generated continuously and/or when shaft 41 is moved along body path axis P-P. Imaging elements 47 may be operable to generate images of body 1 at one or more frequencies of the electromagnetic spectrum, including frequencies in and beyond the visible light range. As shown in FIG. 5, image elements 47 may include digital camera circuits configured to generate two-dimensional graphic images (e.g., photographic, topographic, and the like) of the interior of body 1. For example, the plurality of imaging elements 47 may be spaced apart annularly around an exterior surface of shaft 41 so that the resulting images may be combined to form a continuous panoramic graphical image of the interior of body path 5 and/or body cavity 4.

Plurality of light sources 49 may comprise light emitting diodes configured to generate light at one or more wavelengths. Light sources 49 may be operable with imaging elements 47 (e.g., activated together) to provide illumination for imaging data 43ID. Light sources 49 may be limited to imaging purposes. For example, because tracking sensor 50 may be responsive to a magnetic field, as described below, navigation component 40 may be configured for use in the dark, i.e., without any navigational light, or in the presence of light that might challenge visibility, such as light generated by rapidly pulsed laser energy. In some aspects, plurality of light sources 49 may be configured to generate a photosensitive response from the interior surfaces of body 1.

For example, a photosensitive material may be delivered through lumen 45, body path 5 and/or body cavity 4, and then illuminated by light sources 49 at a wavelength configured to produce a photosensitive reaction with targeted tissues within path 4 and/or cavity 5. In some aspects, characteristics of this reaction (e.g., density, intensity, size, etc.) may be captured by imaging elements 47, output in microscan data 43 as imaging data 43ID, and/or processed by controller 60.

Probe 52 may be operable independent of or together with imaging elements 47 (e.g., activated together) to generate another portion of imaging data 43ID. For example, probe 52 may be configured to direct a wave energy (e.g., light, sound, X-rays, etc.) toward the interior surfaces of body 1, receive a reflected portion of the wave energy, and generate imaging data 43ID including two- or three-dimensional wave energy images of body 1. Probe 52 of FIG. 4, for example, may be an intravascular ultrasound (or "IVUS") probe including a plurality of forward-facing and/or side-facing transducers configured to direct and receive sound waves along path axis P-P and/or in other directions transverse therewith (e.g., FIG. 4A), and generate imaging data 43ID including a plurality of two-dimensional cross-sectional ultrasound images (e.g., FIG. 6A). A representative IVUS ultrasound image of body path 5 is depicted in FIG. 6A, for example, as an axial ultrasound image generated from an IVUS probe. In other aspects, probe 52 may include a laser scanner configured to discharge a laser energy (e.g., a pulsed or continuous laser beam) into body 1, receive a reflected portion of the laser energy, and generate imaging data 43ID including three-dimensional images of path 5 and/or cavity 4.

Tracking sensor 50 may be operable with magnetic field generator 44 to generate location data 43LD, for example, each time at least one of the plurality of imaging elements 47 and/or probe 52 are activated. In FIG. 5, exemplary sensor 50 includes a housing mounted on distal portion 41D of shaft 41, and a sensor coil (not shown) mounted in the housing. Magnetic field generator 44 is shown in FIGS. 1 and 4A-B as a planar element with a plurality of field generation elements (not shown) that may be placed, for example, underneath a bed 8 supporting body 1 (e.g., as in FIG. 1), or directly underneath body 1 (e.g., as in FIGS. 4A-B), and configured to generate a magnetic field (not shown) extending about body path 5. The coil in tracking sensor 50 may output, in real-time, location data 43LD including a continuous locator signal (e.g., an analog signal) responsive to the magnetic field produced by generator 44.

Transceiver 46 may comprise any wired or wireless technology configured to output microscan data 43. For example, transceiver 46 may be configured to output data 43 and/or otherwise communicate with transceiver 66 of controller 60 using any known data communication technology, including Bluetooth®, fiber optic cables, Wi-Fi, and the like. Transceiver 46 of FIG. 2, for example, is coupled to a proximal portion of shaft 41 and located outside of body 1. As shown, transceiver 46 is configured to receive microscan data 43 from internal scanner 42 via a wired connection, and transmit microscan data 43 to transceiver 66 via a wireless connection with controller 60.

Controller 60 of FIG. 7 is configured to generate a pre-operative body information model 25 (e.g., FIG. 3) from macroscan data 23, operatively update model 25 with microscan data 43, and/or output portions of information model 25 in pre-operative or updated state, in real-time, as a navigation image 27 (e.g., FIG. 7). Accordingly, controller 60 may include: one or more processors 62; a memory 65 including computer-readable instructions 64 executable by one or more processors 62; a transceiver 66; sensor interface unit 68; localization unit 70; and a signal station 72.

These elements of controller 60 may be organized in a single device, as shown in FIG. 7, or distributed throughout system 10, each element being capable of reciprocal communication with the next, and/or the components 20 and 40, however arranged. One or more processors 62, for example, may be part of controller 60, distributed throughout system 10, and/or located remotely from system 10 and placed in communication therewith. Processors 62 are configured to perform any computational function described herein responsive to computer-readable instructions 64. Memory 65 may include any technology configured to store instructions 64 as well as any other data and/or information described herein. Like processors 62, memory 65 also may be located anywhere relative to system 10.

Transceiver 66 may comprise any wired or wireless technology configured to receive macroscan data 23 and microscan data 43. For example, transceiver 46 may be configured to receive data 23 and 43, and/or otherwise communicate with transceiver 26 of navigation component 20 and transceiver 46 of navigation component 40 using any known data communication technology, including Bluetooth®, fiber optic cables, Wi-Fi, and the like. Transceiver 66 may be located anywhere relative to system 10.

Processor 60 may be configured to generate location data 43LD any time, such as whenever imaging dating 43ID is generated. For example, sensor interface unit 68 (e.g., FIG. 7) may be configured to receive the locator signal from tracking sensor 50, and convert (e.g., condition, amplify, and/or digitize) the locator signal into a digital location signal including raw magnetic data. Localization unit 70 (e.g., FIG. 7) may be configured to receive the digital location signal, and generate instantaneous location data 43LD based on the raw magnetic data, each time at least when one of the plurality of imaging elements 47 and/or probe 52 are activated. Signal station 72 is configured to output location data 43LD, for example, for display within navigation image 27.

Figure 3:
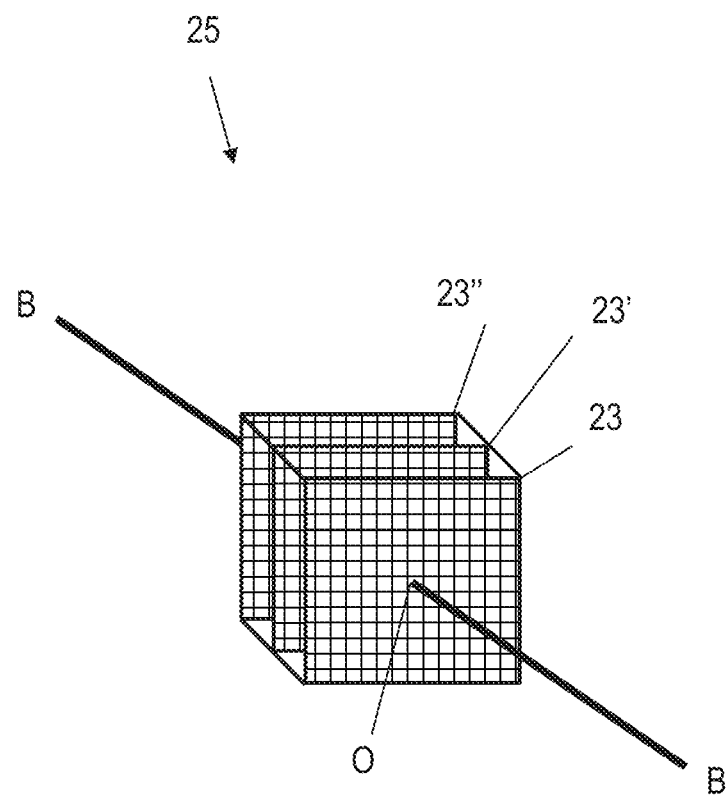
FIG. 3 depicts aspects of an exemplary body information model.

Body information model 25 may be generated with controller 60 by combining two- or three-dimensional images within macroscan data 23 according to location data 23LD to define a three-dimensional data set or data mesh. For example, as shown in FIG. 3, macroscan data 23 may include a first cross-sectional data set 23', a second cross-sectional data set 23'', and a third cross-sectional data set 23''' spaced apart at predetermined intervals along body axis B-B. First data set 23' may be generated by positioning external scanner 22 at a first location along axis B-B, generating imaging data (e.g., 23ID'), and associating location data (e.g., 23LD') therewith. External scanner 22 may then be moved to second and third positions on axis B-B to generate second data set 23'' and third data set 23'''. In this example, controller 60 is configured to generate the three-dimensional data set by combining (e.g., stitching) the images within data sets 23', 23'', and 23''' along body axis B-B. Similar methods may be used to combine three-dimensional data sets.

In other aspects, body information model 25 may be generated by another device and delivered to controller 60 without external scanner 22. For example, information model 25 may be included with the patient's electronic medical records and delivered to processor 60 via transceiver 66. Body information model 25 also may be created with microscan data 43 using similar methods.

Controller 60 may define at least a general representation of body cavity 4, body path 5, and path axis P-P in this three-dimensional data set. For example, controller 60 may automatically define the boundary conditions of body cavity 4 and body path 5, and/or plot body path axis P-P therethrough. To enhance this general representation of body 1, controller 60 is configured to operatively update (e.g., in real-time, during an operation) a pre-operative version of body information model 25 by correlating location data 43LD with location data 23LD at target locations in body 1, and combining imaging data 23ID with a correlated portion of imaging data 43ID at the target locations. For example, because body path axis P-P is defined in model 25, location data 43LD may be correlated with location 23LD by locating a portion of imaging data 43ID at a first location along path axis P-P, geometrically aligning (e.g., resizing, shifting, rotating, etc.) a boundary condition defined by imaging data 23ID at the first location with a boundary condition defined by imaging data 43ID at that location, and then repeating these steps at a plurality of second locations along path axis P-P. A diameter of body path 5 may, for example, be used as the boundary condition.

Imaging data 23ID and 43ID may be combined using a variety of techniques. In one aspect, portions of imaging data 43ID are overlaid onto or stitched together with portions of imaging data 23ID at a plurality of locations along axis P-P. For example, controller 60 may be configured to select a target location in pre-operative body information model 25, identify imaging data 23ID and 43ID associated with the target location, and overlay aspects of data 43ID onto data 23ID at that location. A cross-sectional image included in imaging data 43ID at the target location may, for example, be overlaid onto a cross-sectional image included in imaging data 23ID at the same location. Similarly, a three-dimensional image included in data 431D may be stitched together with a three-dimensional image included in data 231D at the target location.

Body information model 25 may be enhanced by combining imaging data 231D with imaging data 431D. For example, because imaging data 431D may be generated at a higher resolution than imaging data 231D, owing to the different capabilities of scanner 42 and its location within body 1, the resolution of body information model 25 may be increased when imaging data 231D and imaging data 431D are combined. To provide even more detail, controller 60 may be further configured to overlay graphical images captured by the plurality of imaging elements 47 onto representation of body cavity 4 and/or body path 5 in body information model 25, resulting in enhanced or even photorealistic depictions of the interior surfaces cavity 4 and/or path 5. These graphical images may aligned and oriented within body information model 25 (e.g., resized, shifted, rotated, etc.) according to location data 23LD and/or 43LD. If a photosensitive material has been delivered into body path 5, and activated by plurality of light sources 49, for example, then any resulting photosensitive response may thus be represented in body information model 25, allowing for identification and/or diagnosis of those responses. Other conditions may be identified and diagnosed using similar methods, with or without a photosensitive material.

When generated by controller 60 according to these aspects, body information model 25 may be a data-rich environment that is far more detailed than would otherwise be possible with just external scanner 22 or internal scanner 42. To further leverage the capabilities of this environment, controller 60 may be configured to output aspects of model 25 as a two- or three-dimensional navigation image 27. Any aspect of body information model 25 described herein may be represented in image 27. For example, in FIG. 7, navigation image 27 is a three-dimensional representation that has been visually enhanced, for example, by adjusting contrast and color, adding boundary lines, creating a wireframe model, and truncating extraneous anatomy. Any graphical technique may be used. As shown in FIG. 7, for example, controller 60 may use location data 23LD and 43LD to output navigation image 27 as a three-dimensional representation of body 1 depicting external surface 2, entry point 3, interior cavity 4, body path 5, and body path axis P-P in relation to internal scanner 42. For example, cavity 4 of FIG. 7 may be the interior of a kidney, and navigation image 27 may provide a three-dimensional representation depicting scanner 42 moving through a natural body path extending into the kidney through a urethra, bladder, and/or ureter.

Whether two- or three-dimensional, numerous aspects of navigation image 27 may be realized in system 10. For example, controller 60 may be configured to overlay microscan data 43 onto macroscan data 23, and iteratively define the boundaries of body path 5 and/or body cavity 4. These boundaries may then be displayed on navigation image 27 to provide, for example, a highly detailed two- or three-dimensional map of body 1. With reference to these boundaries, controller 60 of FIG. 7 may be configured to plot a course through body path 5, and/or display the course on navigation image 27, for example, as a two- or three-dimensional pathway. Image 27 may be configured to guide shaft 41 through body path 5 along this pathway. For example, because the location of scanner 42 in body 1 may be determined from location data 43ID, navigation image 27 may include graphical indicators (e.g., directional arrows) configured to guide scanner 42 through body path 5 along axis P-P.

Responsive to navigation image 27, a user may guide scanner 42 into a specific portion of body cavity 4 (e.g., a calyx of a kidney) by, for example, manipulating an actuator on the handle of an endoscope so as to articulate and/or advance the distal end 41D of shaft 41 through a tortuous portion of body path 5, and/or around a tight corner inside of cavity 4, as shown by the movements between FIG. 4A and FIG. 4B. Direct visualization of body path 5 may be provided by imaging elements 47, but is not required. For example, image 27 may be used to guide distal end 41D toward a kidney stone located in body cavity 4, even if the stone is located in a narrow calyx and surrounded by a turbid fluid; regardless of bio-impedance changes, respiratory patterns, or fluid status; and without reliance on a positional electrodes or visual images. Controller 60 may be configured to provide additional navigation and cue features to further guide distal end 41D, such as generating audio or tactile feedback signals.

Controller 60 may be configured to identify one or more targeted objects or locations in body 1, and/or determine characteristics of said objects or locations. Navigation image 27 may allow for rotation and zoom, permitting optimal views of the targeted objects or locations; and/or the selection of particular objects or locations. Accordingly, controller 60 may allow a user to plan an operation with navigation image 27, and annotate image 27 during the operation, for example, by marking portions of body cavity 4 that have been treated. As a further example, the wave energy generated by probe 52 may be utilized to identify kidney stones inside of body cavity 4, determine the location of each kidney stone in body information model 25, and ascertain characteristics of each stone (e.g., composition, density, fragility, and/or size).

Controller 60 may be further configured to identify stones having a targeted characteristic, associate the targeted stones with one or more tags or icons in navigation image 27, determine whether a user has removed the targeted stones (or missed one), and/or validate that cavity 4 has been cleared of all the stones. Each targeted stone may, for example, be associated with a different tag or icon to facilitate rapid identification. These tags or icons may indicate a size of the stone, such as a maximum width of the stone. Controller 60 may be configured to compare the maximum width of each stone with a predetermined maximum size of a retrieval device (e.g., the maximum diameter of a retrieval basket or channel), and indicate whether each stone can removed with said device, allowing the user to determine whether additional treatment is required. For example, a stone may be captured in a retrieval basket, sized to determine a maximum width, and associated with a tag or icon indicating whether the captured stone can be removed in said retrieval basket without further treatment. These tags or icons may, for example, indicate whether the captured stone may be removed if released and recaptured to a lower profile orientation, and/or treated with laser energy to decrease the size of the capture stone.

Similar techniques may be used to determine characteristics (e.g., a size, surface area, or volume) of body cavity 4 and/or body path 5, and associate cavity 4 and/or path 5 with said characteristics. For example, various natural markers within body cavity 4 and/or body path 5 may be associated with tags and icons in navigation image 27 to communication the respective volumes of cavity 4 and path 5.

Figure 8A:
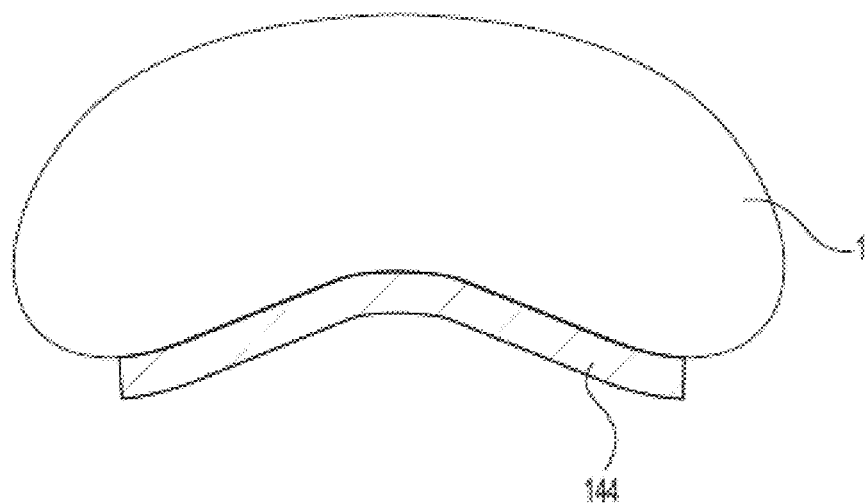
FIG. 8A depicts an exemplary navigation device.
Figure 8B:
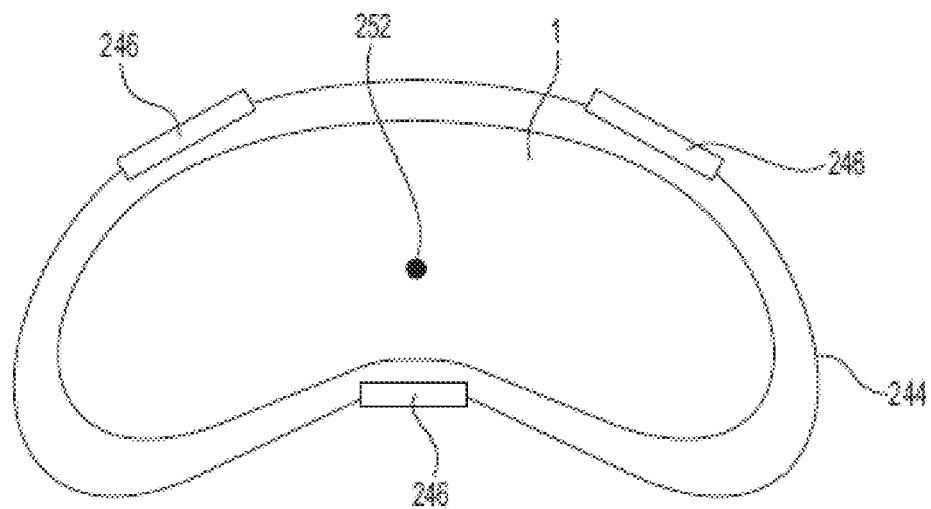
FIG. 8B depicts another exemplary navigation device.

Additional or alternative aspects of navigation component 40 and controller 60 are now described with reference to FIGS. 8A-B. System 10 may include any combination of these aspects with any other aspects described herein, each possible combination being part of the present disclosure.

According to some additional aspects, controller 60 is configured to perform microscan sequences. For example, the plurality of imaging elements 47, plurality of light sources 49, and probe 52 may be activated in a predetermined sequence, and localization unit 70 may generate location data 43LD each time these elements are activated in the predetermined sequence. Accordingly, system 10 may, for example, be switchable between: a first mode with a continuous activation rate corresponding with a desired refresh rate of image 27 (e.g., 60 hz or 120 Hz); a second mode with a pulsed and/or staggered activation rate corresponding with a desired imaging or treatment method (e.g., photosensitive reactions); and/or a third mode where microscan data 43 is automatically generated each time internal scanner 42 is moved a predetermined distance along body path axis P-P (e.g., <1 mm).

Magnetic field generator 44 is depicted as a planar element in FIGS. 1 and 4A-B, but may assume any shape, and include any number of field generation elements. For example, an alternative magnetic field generator 144 is depicted in FIG. 8A as a flexible element that is directly attached (e.g., adhered) to a portion body 1 (e.g., the back) so as to provide a fixed frame of reference for tracking sensor 50, even if body 1 is moved during the time period between each macroscan and/or microscan. Generator 44 also may be formed integral with bed 8 (FIG. 1), which also may provide a reference location for body 1.

In some aspects, tracking sensor 50 is operable with additional and/or alternative tracking devices. For example, sensor 50 may be operable with a sensor belt 244, depicted in FIG. 8B as being wrapped around body 1. As shown, belt 244 includes three external sensors 246, although any number of sensors may be provided. Belt 244 of FIG. 8B is wrapped around a medial-lateral axis of body 1 so that sensors 246 are arranged about body axis B-B of body 1 in a generally triangular formation. In this configuration, sensors 246 may generate location data 43LD for tracking sensor 250 as it moved through an interior diameter of belt 244. For example, in FIG. 5B, tracking sensor 250 includes an RFID sensor or antenna located on a distal portion of an elongated element, and sensors 246 are operable with the RFID sensor to generate location data 43LD when the elongated element is moved through belt 244. Belt 244 may have a narrow width (e.g., 1-3 inches); alternatively, belt 244 may be elongated to define a sleeve. In some aspects, belt 244 includes tension elements (e.g., elastic, buckles, etc.) configured to hold belt 244 in a fixed position relative to body 1.

In still other aspects, internal scanner 42 may include a shape-sensing mechanism configured to determine location data 43LD from the shape of shaft 41. For example, the shape-sensing mechanism may be configured to measure the stress and deflection of elongated shaft 41 at various positions along its length, and determine location data 43LD therefrom independent of any temperature or loading applied to shaft 41. In some aspects, the shape-sensing mechanism may be included within an optical fiber extending within shaft 41, such as a Fiber Bragg Grating (FBG) fiber. Other exemplary shape-sensing fibers may include those sold by Luna Inventions® (see, e.g., Fiber Optic Shape and Position Sensing, available at https://www.youtube-.com/watch?v=Yc8Q-CxvDKU (uploaded on Jan. 14, 2008)); and/or those described in U.S. Patent Publication No. 2014/0257095, filed Mar. 11, 2014, the entireties of which are hereby incorporated by reference.

Although not required, controller 60 may be configured to steer shaft 41 at least partially through body path 5 and/or into body cavity 4 responsive to body information model 25, with or without navigation image 27. For example, shaft 41 may include a plurality of electrically responsive articulation sections, and controller 60 may include a steering module 74 (shown in dotted lines on FIG. 4) configured to generate a steering signal responsive to a user input, such as the movement of a joystick in a proximal or distal direction and/or a confirmation as to location of body cavity 4. Steering module 74 may use the steering signal to selectively actuate the plurality of electrically responsive articulation sections of shaft 41. The user input need not be exact or precise. For example, because body information model 25 includes a detailed three-dimensional data set, steering module 74 may be configured to automatically plot a precise course through a portion of body path 5 responsive to a generic user input (e.g., a forward joystick movement), and/or steer shaft 41 through body path 5 on that course without exact corrections from the user.

Figure 9A:
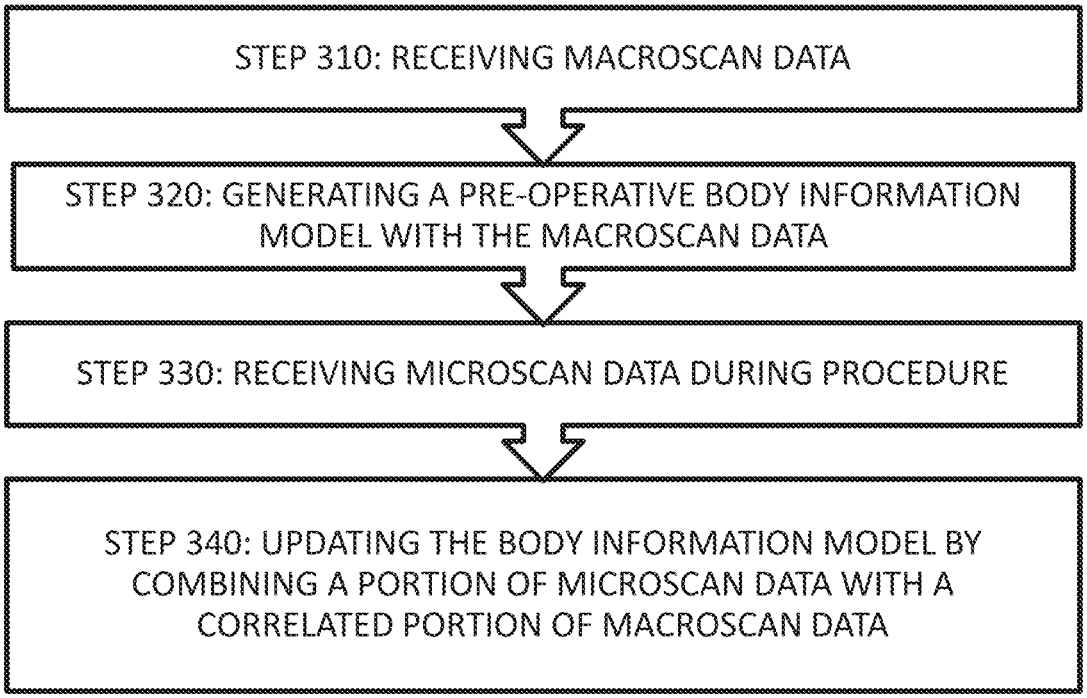
FIG. 9A depicts an exemplary method.
Figure 9B:
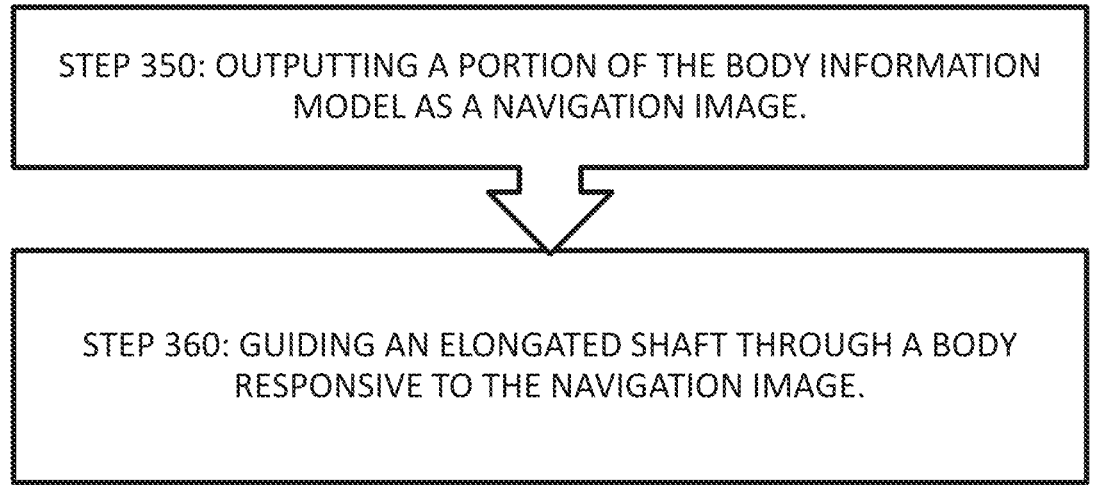
FIG. 9B depicts another exemplary method.

Exemplary methods are depicted in FIGS. 9A-B with reference to various elements of system 10 described herein. Numerous aspects of these methods are now described. According to one aspect, shown in FIG. 9A, an exemplary method 300 may comprise: receiving macroscan data 23 (310); generating a pre-operative body information model 25 with macroscan data 23 (320); receiving microscan data 43 (330) during an operation; and updating the body information model by combining a portion of microscan data 43 with a correlated portion of macroscan data 23 (340).

In method 300, macroscan data 23 may include pre-diagnostic and/or pre-operative images taken in advance of an operation. Each image may be generated by external scanner 22. For example, method 300 at step 310 may further comprise: directing a wave energy (e.g., light, sound, X-rays, etc.) toward exterior surface 2 of body 1, receiving a reflected portion of the wave energy, and generating imaging data 23ID including wave energy images of body 1. The wave energy may be directed along imaging axis I-I, such that each wave energy image includes a cross-sectional image of body 1 (e.g., FIG. 2A). Method step 310 may be repeated at a plurality of positions along body axis B-B of body 1. For example, step 310 may comprise positioning external scanner 22 at a plurality of positions along a body axis B-B of body 1, generating macroscan data 23 including imaging data 23ID and location data 23LD at each of the plurality of positions, and outputting macroscan data 23 to controller 60.

Method 300 at step 320 comprises generating a pre-operative body information model 25 with macroscan data 23. Body 1 may be moved after the macroscans are completed, such that method step 320 may occur anytime after method 310. In keeping with previous examples, method step 320 may comprise combining macroscan data 23 according to location data 23LD to define a three-dimensional data set. Step 320 may further comprise providing at least a general representation of body cavity 4, body path 5, and path axis P-P in this three-dimensional data set.

As noted above, body information model 25 may be generated by another device and deliver to controller 60 without external scanner 22, in which case, method 300 at steps 310 and 300 may comprise receiving model 25 with transceiver 66. For example, method 300 may comprise receiving body information model 25 from a patient's electronic medical record, modifying aspects of model 25 as described herein, and/or updating the electronic medical record accordingly.

Microscan data 43 may include two- or three-dimensional images taken during an operation. Each of these images may be generated by internal scanner 42. For example, because of probe 52, method 300 at step 330 may include: directing a wave energy (e.g., light, sound, X-rays, etc.) toward the interior surfaces of body 1, receiving a reflected portion of the wave energy, and generating imaging data 43ID including wave energy images of body 1. Each wave energy image may, for example, include a cross-sectional image of body path 5 (e.g., FIG. 6A). Graphical images from imaging elements 47 may likewise may be included in imaging data 43ID. Accordingly, method step 330 may comprise positioning internal scanner 42 at a plurality of positions along path axis P-P, generating microscan data 43 including imaging data 43ID and location data 43LD at each of the plurality of positions, and outputting data 43.

Method step 340 of FIG. 9A comprises updating the pre-operative body information model 25 by combining a portion of microscan data 43 with a correlated portion of macroscan data 23. In some aspects, information model 25 is updated in real-time as internal scanner 22 is moved through body 1. For example, step 340 may include: correlating location data 23LD with location data 43LD at a target location in body 1, and combining imaging data 23ID with imaging data 43ID at the target location. Location data 23LD and 43LD may be correlated in body information model 25 using any technique. Any means of combining macroscan data 23 with microscan data 43 may likewise be employed in step 330. For example, a two-dimensional cross-sectional ultrasound image included in imaging data 43ID may be overlaid onto a two-dimensional cross-sectional X-ray image included in imaging data 23ID to update the boundary conditions of body cavity 4 and/or body path 5. Likewise, portions of a three-dimensional image in data 23ID may be overlaid with a two-dimensional image in data 43ID, or stitched together with portions of a three-dimensional image in data 23ID.

Additional steps for method 300 are depicted in FIG. 9B as comprising: outputting a portion of body information model 25 as navigation image 27 (350), and guiding shaft 41 through body 1 responsive to or as function of image 27 (360). Navigation image 27 may be a two- or three-dimensional image generated with any technique. For example, method step 350 may comprise graphically rendering the three-dimensional data set included in body information model 25. Navigation image 27 may be enhanced in step 350. For example, step 350 may comprise associating the boundary conditions of body cavity 4 and/or body path 5 with a particular color or line weight. As a further example, step 350 may further comprise superimposing graphical images from imaging elements 47 onto these boundary conditions.

Method 300 at step 360 may include guiding steps. For example, a plurality of body paths 5 may be defined through body 1, such that method step 360 includes obtaining user input regarding an optimal path 5. Step 360 may further comprise generating one or more graphical indictors (e.g., directional arrows) configured to guide elongated shaft 41 through path 5. Additional navigation and cue features may be provided at step 360, such as generating audio or tactile feedback signals. Additional targets in body 1 may be identified in method 300. For example, step 360 may further include identifying one or more targeted objects or locations in body cavity 4, determining characteristics of said one or more objects or locations, and guiding the distal end 41D of elongated shaft 41 towards a particular object or location based on its characteristics. Although not shown in FIGS. 9A-B, additional method steps may be provided with respect to any aspect of system 10 described herein.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:
1. A method comprising:
receiving macroscan data including first images of a body and first location data associated with each first image;
combining the first images according to the first location data to generate a body information model;
positioning a navigation component in the body;
generating microscan data with the navigation component, the microscan data including second images of the body and second location data associated with each second image;
correlating the first location data with the second location data at a target location in the body information model;
modifying the body information model by combining the first images with the second images at the target location;
outputting a portion of the body information model as a navigation image;

identifying a path through the body in the navigation image;

generating at least one graphical cue configured to guide the navigation component through the path; and guiding the navigation component through the path in response to the navigation image and the at least one graphical cue.

2. The method of claim 1, wherein the navigation component includes a shaft and an internal scanner located on a distal portion of the shaft, and the method further comprises positioning the internal scanner in the body and generating the microscan data with the internal scanner.

3. The method of claim 2, wherein the internal scanner includes a probe configured to generate wave energy images of the body and the second images include the wave energy images, the method further comprising generating the wave energy images with the probe.

4. The method of claim 3, wherein the probe includes one or more ultrasound transducers configured to generate ultrasound images of the body, and generating the wave energy images includes generating ultrasound images with the one or more ultrasound transducers.

5. The method of claim 3, wherein the probe includes one or more laser sources configured to generate laser images of the body, and generating the wave energy images includes generating laser images with the one or more laser sources.

6. The method of claim 2, wherein the internal scanner includes a plurality of imaging elements configured to generate graphical images, and the method comprises generating the graphical images at one or more frequencies of the electromagnetic spectrum with the plurality of imaging elements, and the second images include the graphical images.

7. The method of claim 6, wherein generating the graphical images comprises generating the graphical images in a visual light range.

8. The method of claim 6, wherein the internal scanner includes a plurality of light sources, and the method comprises operating the plurality of light sources independent of or together with the plurality of imaging elements.

9. The method of claim 1, wherein generating the microscan data includes generating second images and location data according to a predetermined sequence.

10. The method of claim 9, wherein the second images are generated at a rate of 60 Hz or greater in the predetermined sequence.

11. The method of claim 1, wherein the navigation component includes a shaft, and positioning a navigation component in the body comprises moving a distal portion of the shaft through the body.

12. The method of claim 11, wherein the distal portion of the shaft includes a tracking sensor responsive to a magnetic field, and generating the second location data comprises moving the tracking sensor in the magnetic field.

13. A method comprising:
receiving macroscan data prior to an operation;
generating a body information model from the macroscan data;
positioning a navigation component in a body during the operation;
generating microscan data with the navigation component;
correlating a location in the macroscan data with a location in the microscan data in the body information model;
modifying the body information model by combining an image in the microscan data with an image in the macroscan data;
outputting a portion of the body information model as a navigation image;
identifying a path through the body in the navigation image;
identifying a location of the navigation component in the navigation image; and
guiding the navigation component along the path in the navigation image.

14. The method of claim 13, further comprising:
locating objects in the body relative to the path; and
guiding the navigation component to the located objects.

15. The method of claim 14, further comprising determining characteristics of the located objects.

16. The method of claim 15, further comprising:
selecting one of the located objects based on its characteristics;
performing a treatment on the selected object; and
modifying the body information model to indicate that the selected object has been treated.

17. A method comprising:
receiving macroscan data prior to an operation, the macroscan data including first images of a body and first location data associated with each first image;
combining the first images according to the first location data to generate a body information model;
positioning a navigation component in the body during the operation;
generating the microscan data with the navigation component, the microscan data including second images of the body and second location data associated with each second image;
correlating the first location data with the second location data at a target location in the body information model;
modifying the body information model by combining the first images with the second images at the target location;
outputting a portion of the body information model as a navigation image;
identifying a path through the body in the navigation image;
identifying a location of the navigation component in the navigation image; and
guiding the navigation component along the path in the navigation image.

18. The method of claim 1, wherein the first images include two-dimensional or three-dimensional images, and the second images include two-dimensional or three-dimensional images.

19. The method of claim 13, further comprising generating one or more indicators configured to guide the navigation component along the path in the navigation image.

20. The method of claim 15, wherein the characteristics of the located objects include composition, density, fragility, and/or size.

* * * * *